United States Patent
Pestano et al.

(10) Patent No.: US 10,422,729 B1
(45) Date of Patent: Sep. 24, 2019

(54) BLOOD SAMPLE SEPARATION DEVICES AND METHODS

(71) Applicant: Biodesix, Inc., Boulder, CO (US)

(72) Inventors: Gary Pestano, Lafayette, CO (US);
Hestia Mellert, Longmont, CO (US);
Nathan Kaiser, Arvada, CO (US);
Maximilian Steers, Denver, CO (US);
Keith Kopitzke, Carlsbad, CA (US);
Sean McHugh, Carlsbad, CA (US);
Luke Richard, Carlsbad, CA (US)

(73) Assignee: BIODESIX, INC., Boulder, CO (US)

( * ) Notice: Subject to any disclaimer, the term of this patent is extended or adjusted under 35 U.S.C. 154(b) by 0 days.

(21) Appl. No.: 16/296,918

(22) Filed: Mar. 8, 2019

(51) Int. Cl.
| G01N 33/49 | (2006.01) |
| B01L 3/00 | (2006.01) |
| G01N 1/40 | (2006.01) |
| B01L 3/02 | (2006.01) |

(52) U.S. Cl.
CPC ............ G01N 1/4005 (2013.01); B01L 3/021 (2013.01); *B01L 2300/041* (2013.01); *B01L 2300/069* (2013.01); *B01L 2300/0609* (2013.01); *B01L 2300/123* (2013.01); *B01L 2400/0406* (2013.01); *G01N 1/405* (2013.01); *G01N 2001/4016* (2013.01)

(58) Field of Classification Search
CPC ......... B01L 2300/0681; B01L 2300/08; B01L 2300/0803; B01L 2300/0809; B01L 3/502; B01L 3/5023; G01N 1/4077; G01N 2001/4088; G01N 33/491
See application file for complete search history.

(56) References Cited

U.S. PATENT DOCUMENTS

| 6,231,815 B1 | 5/2001 | Bainczyk et al. |
| 6,258,045 B1 | 7/2001 | Ray et al. |
| 6,539,817 B2 | 4/2003 | Kozak |
| 6,610,732 B2 | 8/2003 | Ueno |
| 7,618,591 B2 | 11/2009 | Slowey et al. |

(Continued)

FOREIGN PATENT DOCUMENTS

| CN | 202166647 | 7/2011 |
| CN | 105865873 | 5/2016 |
| WO | WO 2017/210218 | 12/2017 |

OTHER PUBLICATIONS

"HemaSpot™-HF Blood Collection Device", retrieved from: https://www.spotonsciences.com/products/hemaspot-hf/ on May 28, 2019.

*Primary Examiner* — Dirk R Bass
(74) *Attorney, Agent, or Firm* — Parker Highlander PLLC

(57) ABSTRACT

The present disclosure relates to devices, methods and kits for blood sample separation and analysis. More particularly, the disclosure relates to devices, methods and kits that rapidly separate a blood sample into uniform solid and liquid phases in a sealed environment. A specific example includes a device with a door coupled to the housing, a blood sample separation medium, a mesh material and a desiccant. In one example, the blood sample separation medium is disposed between the housing and the mesh material, the desiccant is coupled to the door, the desiccant is distal from the mesh material when the door is in a first open position, and the desiccant is proximal to the mesh material when the door is in a second closed position.

20 Claims, 12 Drawing Sheets
(6 of 12 Drawing Sheet(s) Filed in Color)

(56) References Cited

U.S. PATENT DOCUMENTS

| | | |
|---|---|---|
| 7,736,907 B2 | 6/2010 | Blankenstein |
| 8,252,139 B2 | 8/2012 | Pankow |
| 8,435,461 B2 | 5/2013 | Kirby |
| 8,916,110 B2 | 12/2014 | Rodenfels |
| 9,040,236 B2 | 5/2015 | Hill |
| 9,186,097 B2 | 11/2015 | Frey et al. |
| 9,539,572 B2 | 1/2017 | Blankenstein et al. |
| 10,048,251 B2 | 8/2018 | Kim et al. |
| 2016/0313298 A1* | 10/2016 | Wright ................ G01N 33/491 |

* cited by examiner

BLOOD SAMPLE SEPARATION DEVICES AND METHODS

BACKGROUND

I. Field

The present disclosure relates to the fields of blood sample separation and analysis. More particularly, the disclosure relates to devices, methods and kits that rapidly separate a blood sample into uniform solid and liquid phases in a sealed environment.

II. Related Art

Existing techniques for blood sample separation can produce solid and liquid phases that are not uniform and therefore make consistent analysis difficult. In addition, it has been observed that there is an increased likelihood of hemolysis of the red blood cells and migration of hemoglobin the longer the sample separation medium is wet with the sample. Increased hemoglobin content in the separated liquid phase could compromise downstream analysis and analyte detection.

For these reasons, sample separation devices and methods that provide for shorter drying times of the sample and more uniform solid and liquid phases are desired.

SUMMARY

The disclosure describes collection devices, methods and kits that enable field collection of whole blood, and separation of plasma from the blood cells without the need for an intervening step such as centrifugation of the blood specimen. Exemplary embodiments include features and components designed to promote uniform spreading of plasma and quick drying of the sample.

Exemplary embodiments include a device for separating components of a blood sample, where the device comprises: a housing; a door coupled to the housing; a blood sample separation medium; a mesh material; and a desiccant. In certain embodiments, the blood sample separation medium is disposed between the housing and the mesh material; the desiccant is coupled to the door; the desiccant is distal from the mesh material when the door is in a first open position; and the desiccant is proximal to the mesh material when the door is in a second closed position.

In particular embodiments, the door is a first door; the device comprises a second door; and the second door is configured to move from a first open position to allow insertion of the blood sample separation medium into the housing to a second closed position to restrict access to the blood sample separation medium. In some embodiments, the first door is coupled to the housing via a first hinge; and the second door is coupled to the housing via a second hinge. Specific embodiments further comprise a seal configured to lock the second door to the housing. In certain embodiments, the second door comprises an extension configured to extend between blood sample separation medium and the first door when the second door is in the second closed position.

In particular embodiments, the blood sample separation medium comprises a first end, a second end, a first side and a second side; the housing comprises a first side proximal to the first side of the blood sample separation medium; the housing comprises a second side proximal to the second side of the blood sample separation medium; the first side of the housing does not contact the first side of the blood sample separation medium; and the second side of the housing does not contact the second side of the blood sample separation medium. In some embodiments, the mesh material is proximal to the first end of the blood sample separation medium. In specific embodiments, the mesh material comprises open squares that are between 0.10 inches and 0.20 inches square. In certain embodiments, the mesh material comprises open squares that are approximately 0.15 inches by approximately 0.15 inches. In particular embodiments, the mesh material comprises an inert material such as a polyethylene membrane.

Exemplary embodiments include a method of separating components of a blood sample, where the method comprises: obtaining a device comprising a housing; a door coupled to the housing, a desiccant coupled to the door; a blood sample separation medium and a mesh material; where the blood sample separation medium is disposed between the housing and the mesh material. In certain embodiments, the method also comprises: moving the door from a closed position to an open position to allow access to the mesh material, where the desiccant is proximal to the mesh material when the door is in the closed position and where the desiccant is distal to the mesh material when the door is in the open position; applying the blood sample to the mesh material; and moving the door from the open position back to the closed position, where the desiccant is proximal to the mesh material when the door is in the closed position.

In particular embodiments, the blood sample has a volume between 200 μL and 300 μL, and in specific embodiments, the blood sample has a volume of approximately 250 μL. In some embodiments, applying the blood sample to the mesh material comprises applying the blood sample via a disposable pipette. In certain embodiments, the disposable pipette is a dual bulb pipette.

Exemplary embodiments also include a kit comprising: a device as disclosed herein (including for example, a device according to claim 1); a pipette; and a container containing the device according to claim 1 and the pipette. In certain embodiments, the container is a multi-barrier pouch. In particular embodiments, the pipette is a dual bulb pipette. In some embodiments, the pipette is configured to transfer a volume between 200 μL and 300 μL, and in specific embodiments, the pipette in the kit is a disposable pipette.

Exemplary embodiments can be used in a variety of settings, including a physician's office or a patient's home. In particular embodiments, blood extraction can be conducted by qualified phlebotomy professionals, and the blood can be drawn into ethylenediaminetetraacetic acid (EDTA) containing collection tubes. In specific embodiments, approximately 250 μL of blood (approximately 3-4 drops) can be taken from the tube and then applied to the device using a transfer pipette. Specific embodiments disclosed herein can separate the plasma and cellular fractions of the whole blood sample within a four-hour period. Exemplary embodiments of the device do not flood or become saturated with whole blood. Particular embodiments of the device are self-contained to prevent contact with the biologic specimen during shipping and handling.

Specific embodiments include a kit in which the device will be packaged in a Biohazard labeled container, e.g. a "zip-lock" type package, which can be placed inside an outer barrier envelope for ambient shipping to a centralized testing laboratory for analysis (e.g. protein and peptide detection by mass spectrometry, immunoassays and Western Blotting). In certain embodiments, specimens will be typically shipped via a mailing service to a testing laboratory, and the protein biomarkers within the dried plasma are stable for up to 7 days from spotting on the device. In specific embodiments, tolerance of the device and specimen stability within the device over a temperature range of −4° F. to 120° F. is achieved.

In contrast to existing devices and methods, exemplary embodiments of the present disclosure apply a significant amount of desiccant located specifically over where the blood is applied to rapidly dry the blood. It has been observed that there was an increased risk of hemolysis of the red blood cells and migration of hemoglobin the longer the sample separation medium was wet. In contrast to the present disclosure, certain existing devices incorporate a desiccant covering the entire sample separation medium. In exemplary embodiments of the present disclosure, the sample separation medium (e.g. filter paper) is in a moisture-tight enclosure. The filter paper also lays on a flat surface without contacting the sides of the device to improve the uniformity of the plasma separation.

As used herein the specification, "a" or "an" may mean one or more. As used herein in the claim(s), when used in conjunction with the word "comprising", the words "a" or "an" may mean one or more than one.

As used herein the specification, the term "door" includes any movable member that may be moved from a closed position to an open position to allow access to a portion of a device or component of a device.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, for the method being employed to determine the value, or that exists among the study subjects. Such an inherent variation may be a variation of ±10% of the stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

DETAILED DESCRIPTION

Figure 1:
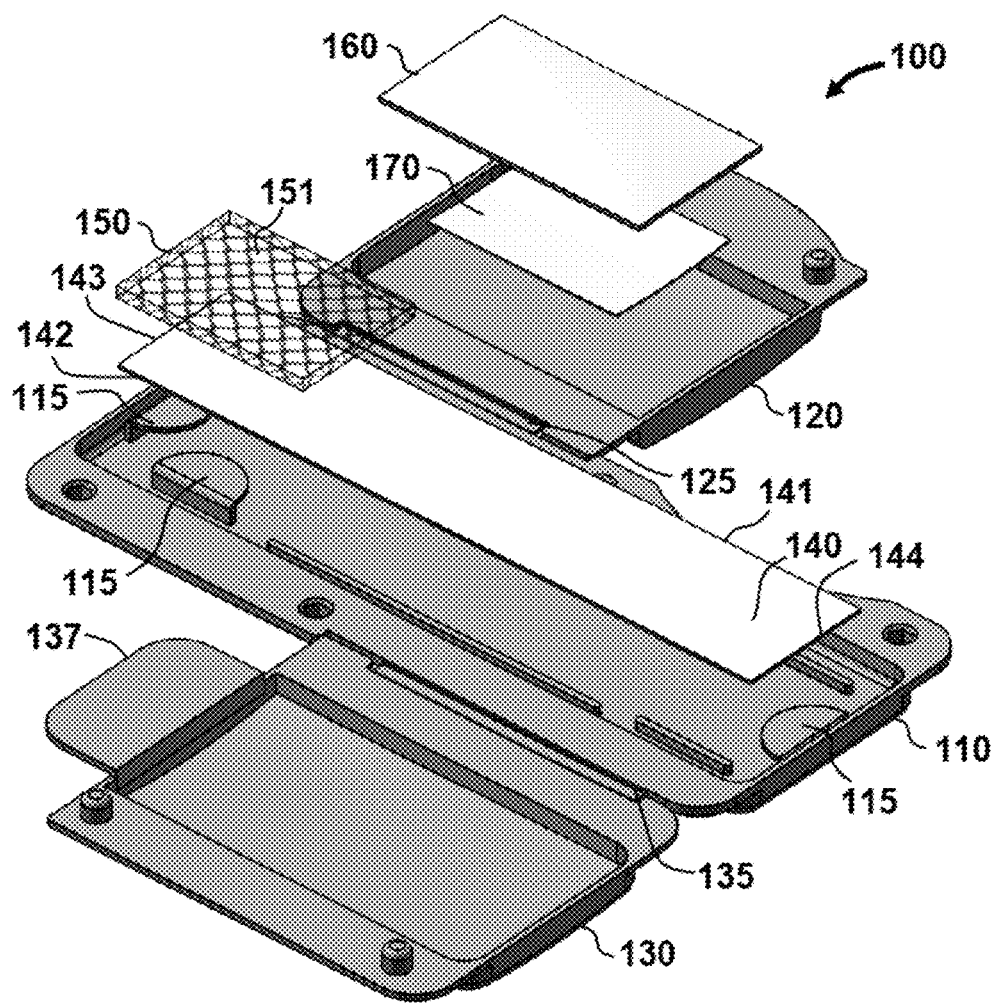
FIG. 1 is an exploded perspective view of a device according to an exemplary embodiment of the present disclosure.

Referring initially to FIGS. 1-4, a device 100 for separating components of a blood sample is shown. In this embodiment, device 100 comprises a housing 110, a first door 120 and a second door 130. Device 100 further comprises a blood sample separation medium 140 and a mesh material 150. In the embodiment shown, first door is coupled to housing 110 via a hinge 125 and second door 130 is coupled to housing 110 via a hinge 135. While a hinged configuration is shown in the figures, it is understood that other embodiments may comprise a different configuration (e.g. sliding, pivoting, etc.) that allow door 120 to be moved to allow access to mesh material 150.

In the illustrated embodiment, blood sample separation medium 140 is configured as a strip with a first side 141, a second side 142, a first end 143 and a second end 144. In the embodiment shown, blood sample separation medium 140 is disposed between housing 110 and mesh material 150, which is proximal to first end 143. Housing 110 may also comprise retaining members 115 (e.g. tabs or other suitable features) to retain blood sample separation medium 140 and mesh material 150 within housing 110.

Figure 2:
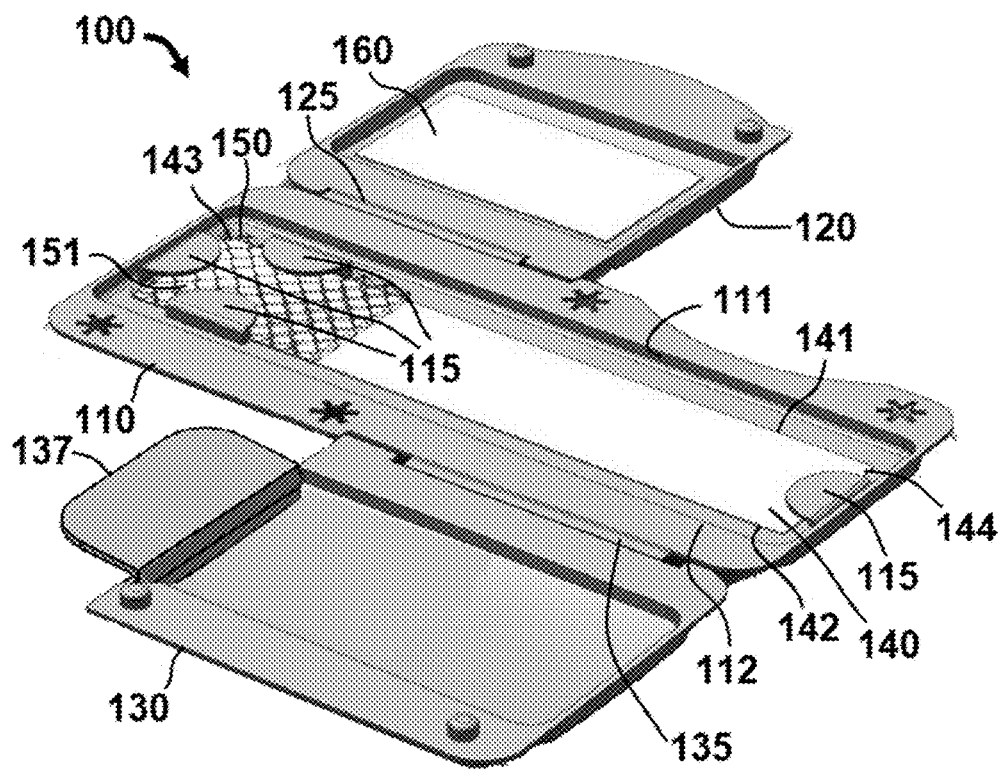
FIG. 2 is a perspective view of the embodiment of FIG. 1 in an open position.
Figure 3:
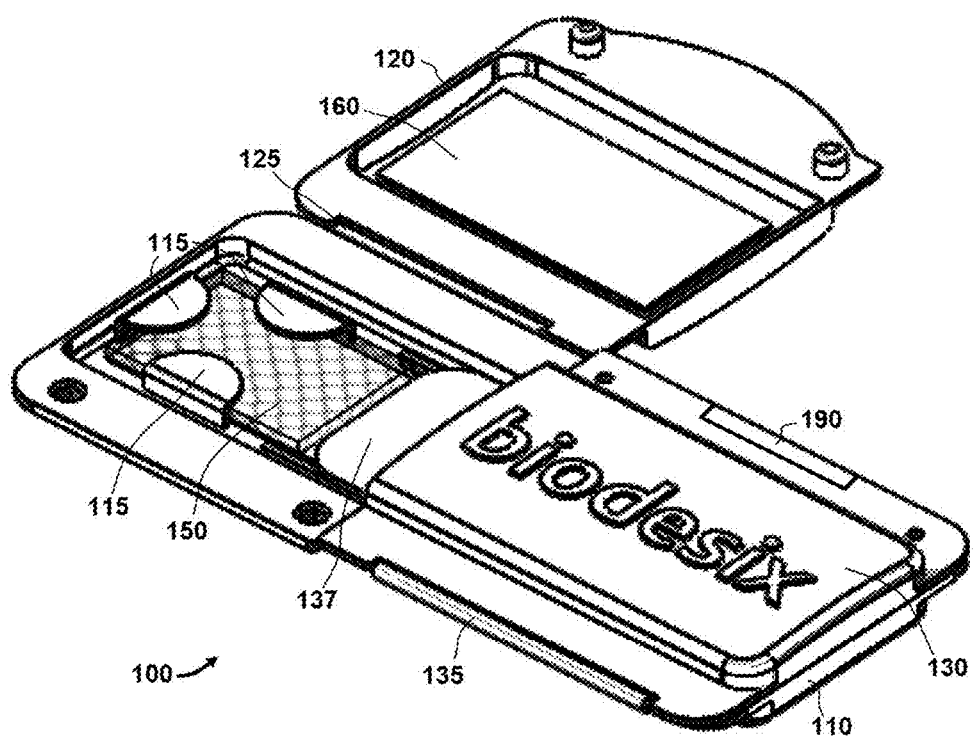
FIG. 3 is a perspective view of the embodiment of FIG. 1 in a partially open position.
Figure 4:
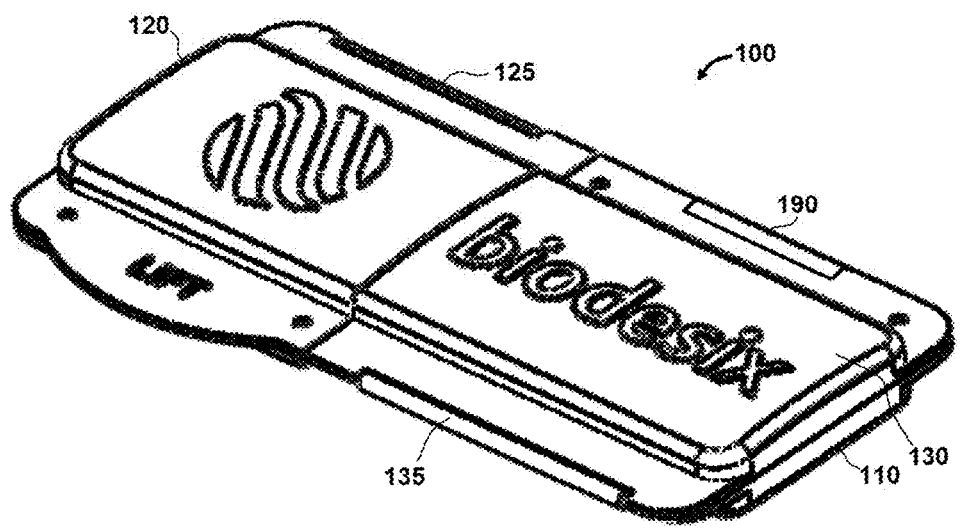
FIG. 4 is a perspective view of the embodiment of FIG. 1 in a closed position.

FIG. 1 illustrates device 100 in an exploded view for purposes of clarity in viewing the individual components. FIG. 2 shows a perspective view of device 100 with first door 120 and second door 130 both in an open position. FIG. 3 shows a perspective view of device 100 with first door 120 in an open position and second door 130 in a closed position, while FIG. 4 shows a perspective view of device 100 with first door 120 and second door in a closed position. In the illustrated embodiment, device 100 further comprises a desiccant 160 coupled to first door 120. In the embodiment shown, desiccant 160 is coupled to first door 120 via an adhesive 170, which may be an adhesive tape or other suitable form of adhesive.

As shown in the figures, when door 120 is an open position shown in FIG. 3, desiccant 160 is in a position that is distal from mesh material 150. When door 120 is in a closed position as shown in FIG. 4, desiccant 160 is moved to a position that is proximal to mesh material 160.

It is understood the use of the term "open" with respect to the position of first door 120 refers to a position in which components (e.g. mesh material 150) within device 100 can be accessed. Conversely, the use of the term "closed" with respect to the position of first door 120 refers to a position in which the components within device 100 are not accessible.

In certain embodiments, device 100 may also comprise a seal 190 configured to maintain second door 130 in a closed position. In the embodiment shown, seal 190 is placed on second door 130 and housing 110 in a position opposite of hinge 135. If second door 130 is opened after seal 190 has been placed on device 100, seal 190 will be broken and thus provide an indication that the integrity of device 100 has been compromised.

During use, device 100 will typically be obtained by a user in the position shown in FIG. 4 (e.g. with both first door 120 and second door 130 in a closed position). The user may the open first door 120 to expose mesh material 150 to the outside environment and allow access to mesh material 150. The user can then place a blood sample onto mesh material 150 and close door 120. Mesh material 150 (and the recently deposited blood sample) are then sealed from the outside environment. Accordingly, with first door 120 in the closed position, mesh material 150, the blood sample, and blood sample separation medium 140 are protected by housing 110, first door 120 and second door 130. In exemplary embodiments, device 100 provides a moisture-tight enclosure for blood sample separation medium 140. Seal 190 restricts a user from opening second door 130. Because second door 130 is not opened by the user, blood sample separation medium 140 is protected from the outside environment and kept dry and clean during transport.

In certain embodiments, device 100 comprises additional features to provide a sealed environment to minimize the risk of contamination during transport. For example, in certain embodiments second door 130 may comprise an extension 137 configured to extend between blood sample separation medium 140 and first door 120 to provide additional sealing capability of device 100. When device 100 is received by the laboratory or other analysis facility, first door 120 can be opened and seal 190 can be broken to open second door 130. Blood sample separation medium 140 can then be removed from device 100 for further testing and analysis. As explained in further detail below, the blood sample can separate into solid/cellular and liquid/plasma phases while device 100 is being transported for analysis.

Figure 5:
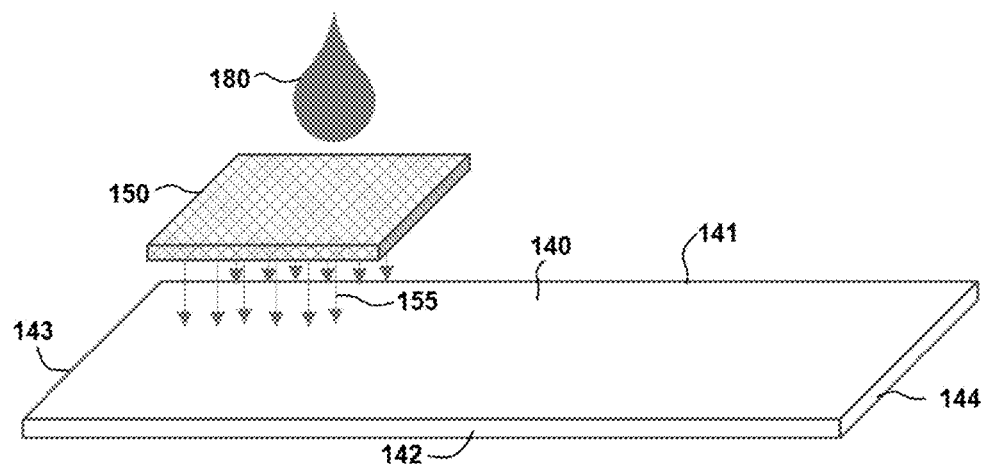
FIGS. 5-7 are perspective schematic view of components of the embodiment of FIG. 1 during use.
Figure 6:
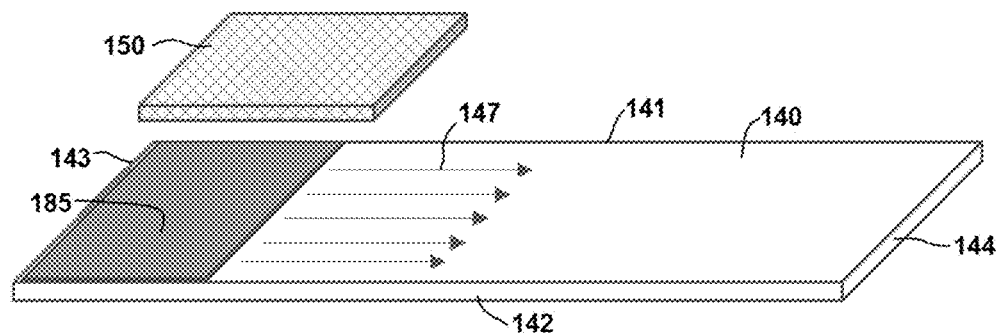
Figure 7:
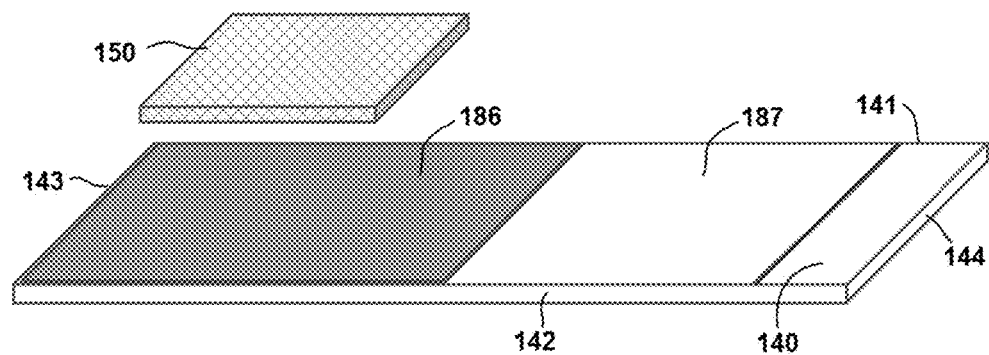

FIGS. 5-7 illustrate schematic views of mesh material 150 and blood sample separation medium 140 during use. While the schematic views in FIGS. 5-7 illustrate mesh material 150 spaced apart from blood sample separation medium 140 for purposes of clarity, it is understood that embodiments of the present disclosure include a configuration in which mesh material 150 is proximal to blood sample separation medium 140. In specific embodiments, mesh material 150 may be in direct contact with blood sample separation medium 140. As shown in FIG. 5, a blood sample 180 is applied to mesh 150 proximal to first end 143 of blood sample separation medium 140. In exemplary embodiments, blood sample 180 is a whole blood sample with a volume between 200 μL and 300 μL. In a specific embodiment, blood sample 180 is a whole blood sample with a volume of 250 μL. When blood sample 180 contacts mesh 150, blood sample 180 is spread across the surface of mesh 150 (e.g. by capillary or wicking action) and contacts blood sample separation medium 140 proximal to first end 143, as indicated by arrows 155. In certain embodiments, mesh material 150 comprises squares 151 that are between 0.10 inches and 0.20 inches square. In specific embodiments, mesh material 150 may be configured as an inert material such as polyethylene membrane comprising open squares that are approximately 0.15 inches by approximately 0.15 inches.

When first door 120 is moved to the closed position, desiccant 160 is placed in close proximity to mesh material 150 and the recently deposited sample. In certain embodiments, desiccant 160 may be in direct contact with mesh material 150 when first door 120 is in the closed position. Accordingly, desiccant 160 can rapidly dry the sample and reduce the likelihood of hemolysis of red blood cells and migration of hemoglobin.

The use of mesh 150 as the initial contact surface for blood sample 180 increases the surface area of blood sample separation medium 140 across which blood sample 180 is distributed (in comparison to a direct application of blood sample 180 to blood sample separation medium 140 without mesh 150). The use of mesh 150 produces a distributed sample layer 185 across blood sample separation medium 140, as shown in FIG. 6.

Referring back now to FIG. 2, blood sample separation medium 140 is narrower than housing 110 in the illustrated embodiment. Accordingly, first side 141 and second side 142 of blood sample separation medium 140 are proximal to—but do not contact—first side 111 and second side 112 of housing 110. The lack of contact between first and second sides 141 and 142 with first and second sides 111 and 112 reduces the effect of "drag" from friction as the blood is being separated by lateral flow (indicated by arrows 147 shown in FIG. 6). Such friction can result in uneven migration patterns with a build-up of red blood cells (RBC) along the edges of the fluid migration zone. With the configuration of device 100, the reduction in drag further permits the even, consistent migration interface across the fluid migration zone. The result is a uniform solid (e.g. cellular) phase 186 and fluid (e.g. plasma) phase 187 on blood sample separation medium 140 as shown in FIG. 7. In the illustrated embodiment, fluid phase 187 does not extend to second end 142 of blood sample separation medium 140. In addition, the ability to place desiccant 160 proximal to mesh 150 after sample 180 has been applied (e.g. by moving first door 120 to the closed position) can reduce the amount of time needed to dry sample 180.

Once received at a central lab, small punches (3-6 mm diameter) can be taken from fluid phase 187 portion of blood sample separation medium 140. In specific embodiments, punches can be submerged into water to elute the plasma proteins. Eluted proteins can then be analyzed in a mass spectrometer with no further fractionation or sample cleanup. The eluted proteins can be resuspended in water, mixed 1 to 1 by volume in a MALDI matrix solution (50% water/50% acetonitrile/0.1% TFA saturated with sinapinic acid), spotted on a metal target and then have their relative abundances recorded after laser excitation in the mass spectrometer. Mass spectrometry is a sensitive technique designed to measure a broad distribution of proteins across a large dynamic range of intensities. Therefore, minimal interferences or contribution to the mass spectra from the collection/separation media in the device is desired.

Figure 8:
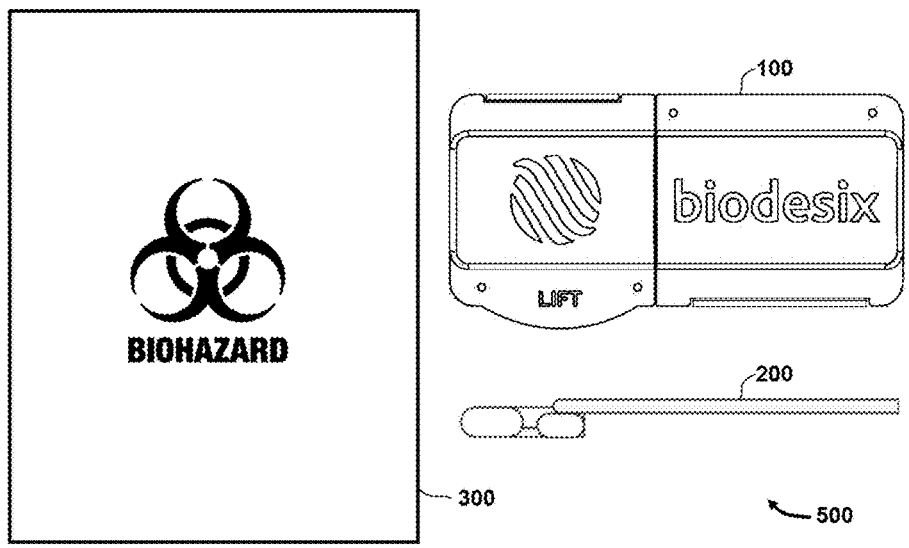
FIG. 8 is a front view of a kit according to an exemplary embodiment of the present disclosure.

Certain embodiments include a kit comprising device 100. Referring now to FIG. 8, a kit 500 comprises a sealed container 300 containing device 100 and a pipette 200. In particular embodiments, sealed container 300 is a multi-barrier pouch with a biohazard label. In specific embodiments pipette 200 is a disposable dual bulb transfer pipette configured to transfer a specific volume of blood to device 100 in the manner previously described herein. In a particular embodiment, pipette 200 is configured to transfer 250 µl of blood to device 100.

Figure 9:
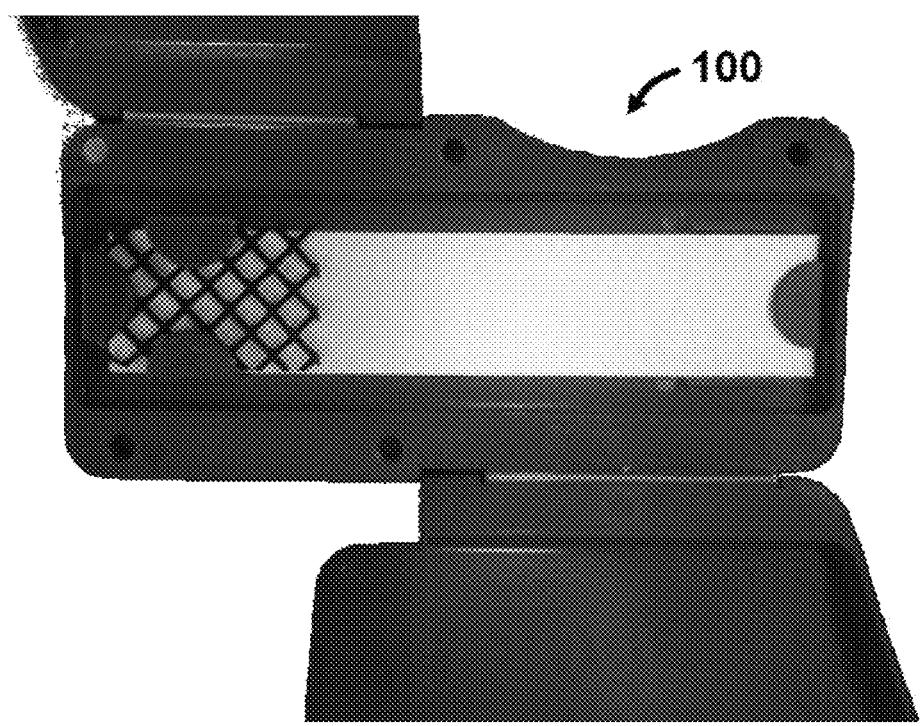
FIG. 9 is a photograph of the embodiment of FIG. 1 with both doors in the open position.
Figure 10:
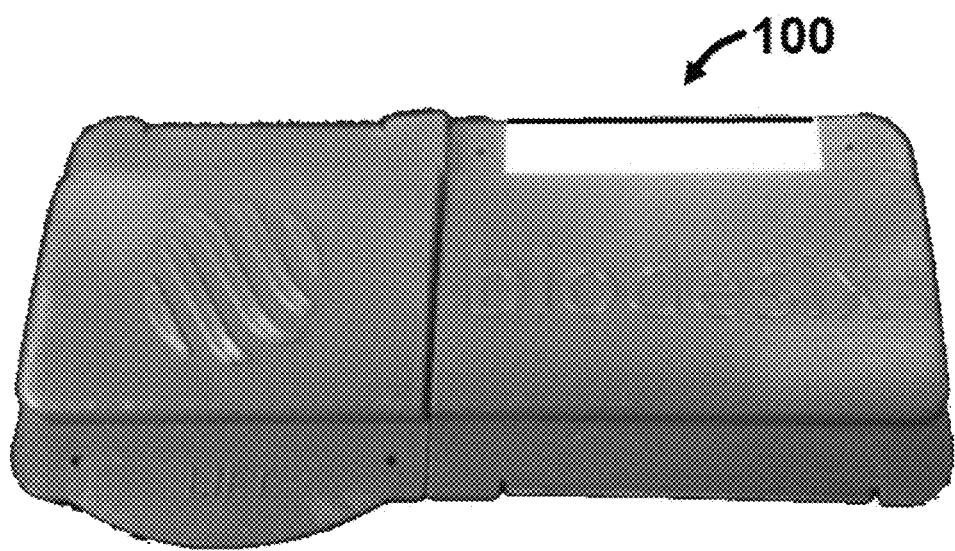
FIG. 10 is a photograph of the embodiment of FIG. 1 with both doors in the closed position.
Figure 11:
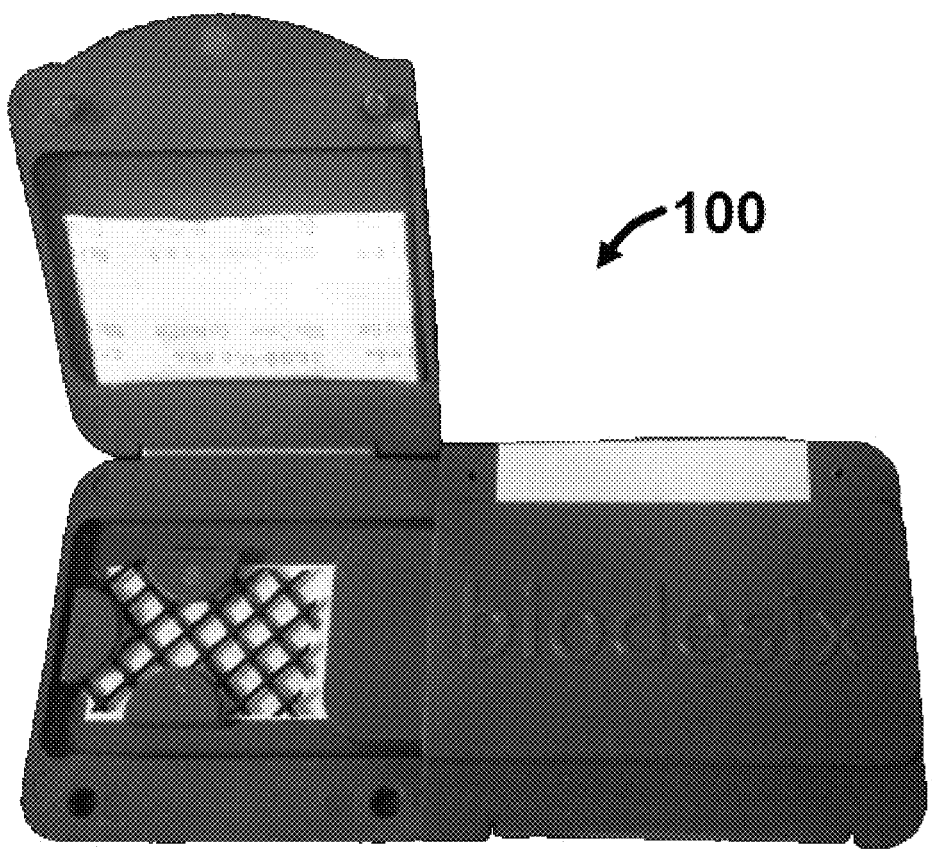
FIG. 11 is a photograph of the embodiment of FIG. 1 with the first door in the open position prior to blood application.
Figure 12:
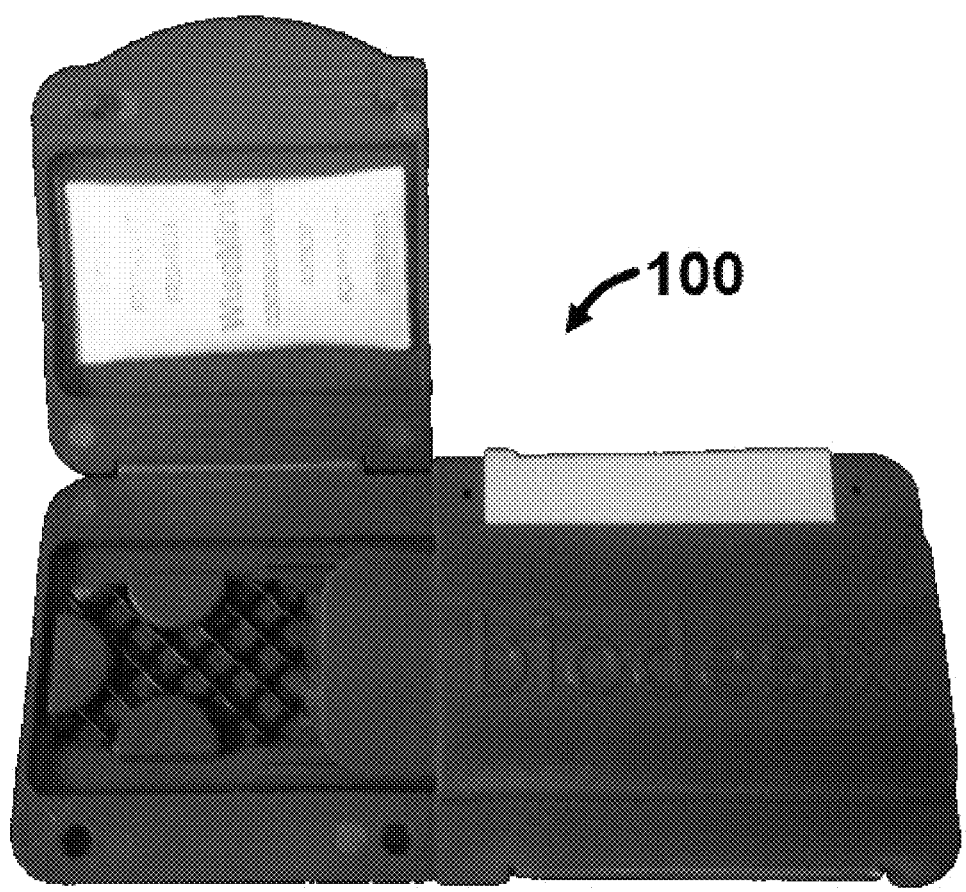
FIG. 12 is a photograph of the embodiment of FIG. 1 with the first door in the open position post blood application.
Figure 13:
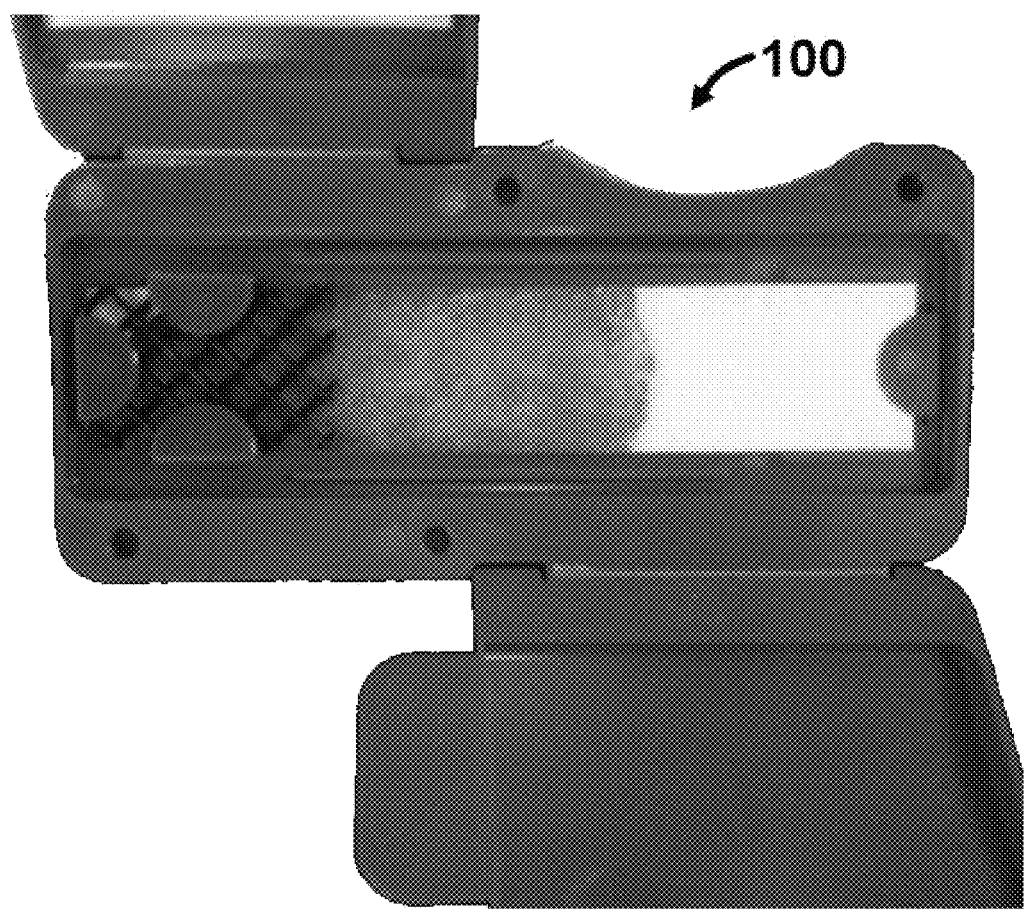
FIG. 13 is a photograph of the embodiment of FIG. 1 with both doors in open position post blood application.

Referring now to FIGS. 9-13, photographs of an exemplary embodiment of device 100 during assembly and use are shown. In FIG. 9, device 100 is shown partially assembled with first door 120 and second door 130 in an open position. This configuration would be before second door 130 is closed and sealed prior to sending to a user. In FIG. 10, device 100 is shown with first door 120 and second door 130 in a closed position, with second door 130 sealed via seal 190. This is the configuration in which a user would receive device 100. Referring now to FIG. 11, device 100 is shown with first door 120 open prior to a sample being deposited onto mesh material 150 by a user. Referring now to FIG. 12, device 100 is shown after a sample has been deposited onto mesh material 150, with first door 120 open. Referring now to FIG. 13, device 100 is shown with first door 120 open and second door 130 open (after seal 190 has been broken). This is the configuration for device 100 when a laboratory or other analyst is preparing to remove blood sample separation medium 140 from device 100 for analysis.

Figure 14:
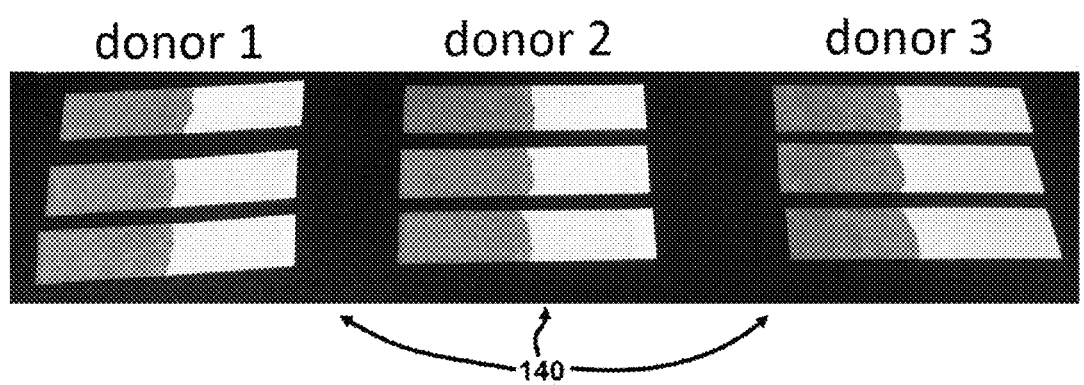
FIG. 14 is a photograph of separation media from 3 donors performed in triplicate removed from the embodiment of FIG. 1.

FIG. 14 illustrates the consistent and uniform separation of the solid/cellular phase from the liquid/plasma phase of a sample for three different blood donors performed in triplicate.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 6,106,732
U.S. Pat. No. 6,231,815
U.S. Pat. No. 6,258,045
U.S. Pat. No. 6,539,817
U.S. Pat. No. 7,618,591
U.S. Pat. No. 7,736,907
U.S. Pat. No. 8,252,139
U.S. Pat. No. 8,435,461
U.S. Pat. No. 8,916,110
U.S. Pat. No. 9,040,236
U.S. Pat. No. 9,186,097
U.S. Pat. No. 9,539,572
U.S. patent Ser. No. 10/048,251
U.S. Patent Publication 20160313298
PCT Patent Publication WO2017210218
CN105865873
CN202166647
https://www.spotonsciences.com/products/hemaspot-hf/

What is claimed:

1. A device for separating components of a blood sample, the device comprising:
a housing;
a door coupled to the housing;
a blood sample separation medium;
a mesh material; and
a desiccant, wherein:
the blood sample separation medium is disposed between the housing and the mesh material;
the desiccant is coupled to the door;
the desiccant is distal from the mesh material when the door is in a first open position; and
the desiccant is proximal to the mesh material when the door is in a second closed position.

2. The device of claim 1, wherein:
the door is a first door;
the device comprises a second door; and
the second door is configured to move from a first open position to allow insertion of the blood sample separation medium into the housing to a second closed position to restrict access to the blood sample separation medium.

3. The device of claim 2 wherein:
the first door is coupled to the housing via a first hinge; and
the second door is coupled to the housing via a second hinge.

4. The device of claim 2 further comprising a seal configured to lock the second door to the housing.

5. The device of claim 2 wherein the second door comprises an extension configured to extend between blood sample separation medium and the first door when the second door is in the second closed position.

6. The device of claim 1 wherein:
the blood sample separation medium comprises a first end, a second end, a first side and a second side;
the housing comprises a first side proximal to the first side of the blood sample separation medium;
the housing comprises a second side proximal to the second side of the blood sample separation medium;
the first side of the housing does not contact the first side of the blood sample separation medium; and
the second side of the housing does not contact the second side of the blood sample separation medium.

7. The device of claim 1 wherein the mesh material is proximal to the first end of the blood sample separation medium.

8. The device of claim 1 wherein the mesh material comprises open squares that are between 0.10 inches and 0.20 inches square.

9. The device of claim 1 wherein the mesh material comprises open squares that are approximately 0.15 inches by approximately 0.15 inches.

10. The device of claim 1 wherein the mesh material comprises an inert material such as a polyethylene membrane.

11. A method of separating components of a blood sample, the method comprising:
obtaining a device comprising:
a housing;
a door coupled to the housing;
a desiccant coupled to the door;
a blood sample separation medium; and a mesh material, wherein the blood sample separation medium is disposed between the housing and the mesh material;

moving the door from a closed position to an open position to allow access to the mesh material, wherein the desiccant is proximal to the mesh material when the door is in the closed position and wherein the desiccant is distal to the mesh material when the door is in the open position;

applying the blood sample to the mesh material; and moving the door from the open position back to the closed position, wherein the desiccant is proximal to the mesh material when the door is in the closed position.

12. The method of claim 11 wherein the blood sample has a volume between 200 μL and 300 μL.

13. The method of claim 11 wherein the blood sample has a volume of approximately 250 μL.

14. The method of claim 11 wherein applying the blood sample to the mesh material comprises applying the blood sample via a disposable pipette.

15. The method of claim 14 wherein the disposable pipette is a dual bulb pipette.

16. A kit comprising:
a device according to claim 1;
a pipette; and
a container containing the device according to claim 1 and the pipette.

17. The kit of claim 16 wherein the container is a multi-barrier pouch.

18. The kit of claim 16 wherein the pipette is a dual bulb pipette.

19. The kit of claim 16 wherein the pipette is configured to transfer a volume between 200 μL and 300 μL.

20. The kit of claim 16 wherein the pipette is a disposable pipette.

* * * * *